United States Patent

Braun

Patent Number: 6,136,807
Date of Patent: Oct. 24, 2000

[54] COMPOSITION FOR THE TRANSDERMAL DELIVERY OF LERISETRON

[75] Inventor: Franz-Josef Braun, Borken, Germany

[73] Assignee: 3M Innovative Properties Company, St. Paul, Minn.

[21] Appl. No.: 09/419,859

[22] Filed: Oct. 19, 1999

Related U.S. Application Data

[60] Provisional application No. 60/107,850, Nov. 10, 1998.

[51] Int. Cl.$^7$ .......................... A61K 31/495; A61K 9/70
[52] U.S. Cl. ............................. 514/254; 424/449
[58] Field of Search ............... 514/254; 424/449

[56] References Cited

U.S. PATENT DOCUMENTS

| | | | |
|---|---|---|---|
| Re. 24,906 | 12/1960 | Ulrich | 206/59 |
| 3,786,116 | 1/1974 | Milkovich . | |
| 3,842,059 | 10/1974 | Milkovich et al. . | |
| 4,732,808 | 3/1988 | Krampe et al. | 428/355 |
| 5,011,928 | 4/1991 | Venero et al. . | |
| 5,051,510 | 9/1991 | Venero et al. . | |
| 5,256,665 | 10/1993 | Orjales-Venero et al. | 514/254 |
| 5,322,850 | 6/1994 | Orjales-Venero . | |
| 5,672,604 | 9/1997 | Orjales-Venero . | |

FOREIGN PATENT DOCUMENTS

| | | |
|---|---|---|
| WO 96/08229 | 3/1996 | WIPO . |
| 99/17755 | 4/1999 | WIPO . |

*Primary Examiner*—Raymond Henley, III
*Attorney, Agent, or Firm*—MarySusan Howard; Ted K. Ringsred; Robert W. Sprague

[57] ABSTRACT

The present invention provides a transdermal drug delivery composition comprising:

(a) a copolymer of one or more (meth)acrylate monomers being selected from the group consisting of alkyl acrylates containing 4 to 12 carbon atoms in the alkyl group and alkyl methacrylates containing 4 to 12 carbon atoms in the alkyl group and one or more hydrophilic monomers being copolymerizable with said (meth)acrylate monomers, and (b) a therapeutically effective amount of lerisetron. The transdermal drug delivery composition is used to make a transdermal drug delivery device for the delivery of lerisetron.

21 Claims, No Drawings

COMPOSITION FOR THE TRANSDERMAL DELIVERY OF LERISETRON

This claims priority to Provisional Ser. No. 60/107,850, filed Nov. 10, 1998.

FIELD OF THE INVENTION

The present invention relates to a transdermal drug delivery composition containing lerisetron. The invention further relates to a transdermal delivery device for the delivery of lerisetron.

BACKGROUND OF THE INVENTION

Transdermal drug delivery devices are designed to deliver a therapeutically effective amount of drug across the skin of a patient. Transdermal drug delivery devices typically involve a carrier (such as a liquid, gel, or solid matrix, or a pressure sensitive adhesive) into which the drug to be delivered is incorporated. Devices known to the art include reservoir type devices involving membranes that control the rate of drug release to the skin and devices involving a dispersion of the drug in a matrix such as a pressure sensitive adhesive. The skin, however, presents a substantial barrier to ingress of foreign substances into the body. It is therefore often desirable or necessary to incorporate certain materials that enhance the rate at which the drug passes through the skin. However, the type of device, suitable components for use in the device, the transdermal flux rate that is suitable, and the suitable formulation components are dependent upon the particular drug to be delivered.

Lerisetron (1-(phenylmethyl)-2-(1-piperazinyl)-1H-benzimidazole) is a known compound disclosed in U.S. Pat. No. 5,256,665. Lerisetron is a serotonin $5HT_3$ antagonist. Such antagonists are known to be effective in preventing the nausea and emesis induced by cancer chemotherapy. Other indications for the use of lerisetron include the prophylaxis and treatment of migraine, anxiety and other neuralgic disorders.

SUMMARY OF THE INVENTION

The present invention provides a transdermal drug delivery composition comprising:

(a) a copolymer of one or more (meth)acrylate monomers being selected from the group consisting of alkyl acrylates containing 4 to 12 carbon atoms in the alkyl group and alkyl methacrylates containing 4 to 12 carbon atoms in the alkyl group and one or more hydrophilic monomers being copolymerizable with said (meth)acrylate monomers, and (b) a therapeutically effective amount of lerisetron.

The present invention further provides a transdermal drug delivery device comprising a backing having adhered to one surface a transdermal drug delivery composition comprising:

(a) a copolymer of one or more (meth)acrylate monomers being selected from the group consisting of alkyl acrylates containing 4 to 12 carbon atoms in the alkyl group and alkyl methacrylates containing 4 to 12 carbon atoms in the alkyl group and one or more hydrophilic monomers being copolymerizable with said (meth)acrylate monomers, and (b) a therapeutically effective amount of lerisetron.

The transdermal drug delivery device of the present invention can be used for the treatment or prevention of nausea and emesis, migraine, anxiety or other neuralgic disorders.

DETAILED DESCRIPTION OF THE INVENTION

The transdermal drug delivery composition of the present invention comprises a copolymer of alkyl (meth)acrylate monomers in which the alkyl group has 4 to 12 carbon atoms and hydrophilic monomers that are copolymerizable therewith.

Hydrophilic monomers that are useful in connection with the present invention are typically monomers that have a tendency to bind or absorb water and are preferably monomers of which a homopolymer shows a tendency to swell or dissolve in water. Typically, the hydrophilic monomers contain at least one functional group selected from the group consisting of hydroxy, amino, sulfonamido, urea, carbamate, carboxamido, oxy, carboxylic acid and polyoxyalkylene group. Examples of hydrophilic monomers include N-vinyl-2-pyrrolidone, vinylimidazoles, hydroxyalkyl(meth)acrylates having 2 to 4 carbon atoms in the alkyl group such as 2-hydroxyethylacrylate, mono acrylates of poly (alkyleneoxide), mono methacrylates of poly (alkyleneoxide), alkoxyethylacrylates containing 1 to 4 carbon atoms in the alkoxy group, 2-ethoxyethoxyethyl acrylate, furfuryl methacrylate, furfuryl acrylate, tetrahydrofurfuryl acrylate, tetrahydrofurfuryl methacrylate, propyleneglycol monomethacrylate, glyceryl acrylate, acrylamides, methacrylamides, alkyl substituted acrylamides containing 1 to 8 carbon atoms in the alkyl group, diacetone acrylamide, dialkylacrylamides having 1 or 2 carbon atoms in the alkyl group, N-vinyl-N-methyl acetamide, N-vinyl valerolactam, N-vinyl caprolactam, glycidyl methacrylate, vinyl acetate, tetra-alkylammonium containing monomers such as (meth) acryloxyethyl trimethylammonium chloride, (meth) acryloxyethyl triethylammonium chloride, (meth) acrylamido-ethyl trimethyl ammonium chloride and amino group containing monomers such as dimethylaminoethyl (meth)acrylate, diethylamino(meth)acrylate, morpholinoethyl(meth)acrylate, piperidino-ethyl(meth)acrylate, piperidino-ethyl-(meth)acrylamide, dimethylamino-ethyl (meth)acrylamide and diethylamino-ethyl(meth)acrylamide. Particularly preferred are N-vinyl-2-pyrrolidone and 2-hydroxyethylacrylate.

Additional hydrophilic monomers for use in the copolymer include carboxylic acid group containing monomers such as, for example, acrylic acid and methacrylic acid. However, it is preferred that the amount of recurring units derived from acid group containing monomers is limited to not more than 5% by weight of the copolymer. Most preferably, the copolymer is free of units derived from acid group containing monomers.

The (meth)acrylate monomer(s) of the copolymer are alkylacrylate or alkylmethacrylate monomers containing 4 to 12 carbon atoms in the alkyl group. The alkyl group of the alkyl(meth)acrylate monomer can be linear or branched and may comprise a cyclic group. Examples of the $C_4$–$C_{12}$ alkyl(meth)acrylate monomers include n-butyl, n-pentyl, n-hexyl, cyclohexyl, isoheptyl, n-nonyl, n-decyl, isohexyl, isobornyl, 2-ethyloctyl, isooctyl, n-octyl and 2-ethylhexyl acrylates and methacrylates. Preferred alkyl acrylates include isooctyl acrylate, 2-ethylhexyl acrylate, cyclohexyl acrylate and n-butyl acrylate. Isooctyl acrylate is most preferred.

The copolymer may further comprise units that are derived from monomers other than the $C_4$–$C_{12}$ alkyl(meth) acrylate monomers and hydrophilic monomers. Examples of other monomers that can be copolymerized with the $C_4$–$C_{12}$ alkyl(meth)acrylate monomers and hydrophilic monomers include styrene and short chain $C_1$–$C_3$ alkyl acrylates and methacrylates such as ethyl(meth)acrylate and methyl(meth) acrylate, as wellas units derived from macromonomers that are copolymerizable with the $C_4$–$C_{12}$ alkyl(meth)acrylate monomers and hydrophilic monomers.

In a particularly preferred embodiment of the present invention, the copolymer further comprises units derived from a macromonomer that is copolymerizable with the $C_4$–$C_{12}$ alkyl(meth)acrylate monomers and hydrophilic monomers. The macromonomer preferably corresponds to the general formula:

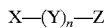

wherein X represents a group copolymerizable with the $C_4$–$C_{12}$ alkyl(meth)acrylate monomers and hydrophilic monomers such as, for example, an ethylenically unsaturated group; Y is a divalent linking group; n is zero or 1; and Z represents a monovalent macromonomer, preferably a substantially linear macromonomer, having a weight average molecular weight in the range of about 500 to 500,000, preferably 2,000 to 100,00, and most preferably 5,000 to 30,000.

Suitable macromonomers include polymethylmethacrylate, styrene/acrylonitirle, polyether and polystyrene macromonomers. Such macromonomers are known and may be prepared according to the methods disclosed in U.S. Pat. No. 3,786,116, U.S. Pat. No. 3,842,059 (both to Milkovich et al.) and U.S. Pat. No. 4,732,808 (Krampe), the disclosure of which are incorporated herein by reference. Furthermore, certain macromonomers are commercially available. For example, polymethylmethacrylate macromonomers suitable for use in this invention are commercially available under the trade designation "ELVACITE" by ICI Acrylics (e.g., ELVACITE 1010, a polymethylmethacrylate macromonomer having an inherent viscosity of 0.070–0.080, a $T_g$ of 105° C., a GPC weight average molecular weight of 7,000–10,000, a GPC number average molecular weight of 2,500–4,000, and a polydispersity of 2.5–3.0, and ELVACITE 1020, a polymethylmethacrylate macromonomer having an inherent viscosity of 0.085–0.10, a $T_g$ of 105° C., a GPC weight average molecular weight of 12,000–15,000, a GPC number average molecular weight of 4,600–6,000, and a polydispersity of 2.5–3.0).

Particularly suitable copolymers for use in the present invention comprise between 55 and 90 percent by weight of units derived from $C_4$–$C_{12}$ alkyl(meth)acrylate monomers, between 7 and 40 percent by weight of units derived from hydrophilic monomers, and between 1 and 7 percent by weight of macromonomers. More preferably, the copolymer comprises between 70 and 80 percent by weight of units derived from $C_4$–$C_{12}$ alkyl(meth)acrylate monomers, between 15 and 25 percent by weight of units derived from hydrophilic monomers, and between 2 and 5 percent by weight of macromonomers.

The copolymers described above can be prepared by methods well known to those skilled in the art and described for example, in U.S. Patent No. RE 24,906 (Ulrich), U.S. Pat. No. 4,732,808 (Krampe), and International Publication Number WO 96/08229, the disclosures of which are incorporated herein by reference.

Lerisetron is present in a transdermal drug delivery composition of the invention in a therapeutically effective amount, i.e., an amount effective to allow the composition to deliver sufficient lerisetron to achieve a desired therapeutic result in the treatment of a condition. The amount that constitutes a therapeutically effective amount varies according to the condition being treated (e.g., nausea and emesis associated with cancer chemotherapy, migraine, etc.), any drugs being coadministered with lerisetron, desired duration of treatment, the surface area and location of the skin over which the composition is to be placed, and the selection of penetration enhancers and other components of the transdermal drug delivery composition. Accordingly, it is not practical to enumerate particular preferred amounts but such can be readily determined by those skilled in the art with due consideration of these and other appropriate factors. Generally, however, lerisetron is present in the transdermal drug delivery composition in an amount of about 2 to about 20 percent, preferably about 5 to about 10 percent by weight based on the total weight of the transdermal drug delivery composition. Preferably the lerisetron is dissolved in the composition. In a more preferred embodiment, the composition is substantially free of solid undissolved lerisetron, and in a particularly preferred embodiment, the composition contains no solid undissolved lerisetron.

The transdermal drug delivery composition preferably also contains one or more agents known to accelerate the delivery of the drug through the skin. These agents have been referred to in the art as penetration enhancers, accelerants, adjuvants, and sorption promoters, and are collectively referred to herein as "enhancers". Some examples of enhancers are polyhydric alcohols, in particular alkane polyols such as dipropylene glycol, propylene glycol, 1,3-butane diol and polyethylene glycol; polyethylene glycol ethers and fatty ethers such as cetyl ether and oleyl ether, polyoxyethylene (4) lauryl ether, polyoxyethylene (2) oleyl ether and polyoxyethylene (10) oleyl ether sold under the trademarks Brij 30, 93 and 97 by ICI Americas, Inc; fatty acid esters such as isopropyl myristate, propyl oleate, ethyl oleate, and isopropyl palmitate; fatty alcohols such as oleyl alcohol, decanol, lauryl alcohol, 1-nonanol and n-octanol; fatty acids such as caprylic acid, lauric acid, oleic acid, palmitate acid, stearic acid and linoleic acid; and $C_5$–$C_{18}$ alkyl esters of a carboxylic acid such as, for example, octyl acetate and pentyl acetate.

Preferred enhancers include fatty acids, in particular oleic acid and lauric acid, fatty acid esters, in particular isopropyl myristate, and polyhydric alcohols, in particular propylene glycol, and mixtures thereof. A particularly preferred enhancer for use in the invention comprises oleic acid in combination with propylene glycol.

The enhancer is dispersed, preferably uniformly dispersed, and more preferably dissolved in a composition of the invention. The enhancer is present in an amount that enhances lerisetron penetration through the skin as compared to a like composition not containing the enhancer when this phenomenon is measured using the skin penetration model described below. The total amount of enhancer used is between 10 and 50 percent by weight and more preferably between 20 and 35 percent by weight of the transdermal drug delivery composition.

The transdermal drug delivery composition may contain additional conventional components such as, for example, crystallization inhibitors, stabilizers and antioxidants. In a preferred embodiment, a base may be added to the transdermal drug delivery composition to adjust the pH. The latter is particularly advantageous when a fatty acid is included in the composition as a penetration enhancer. Examples of suitable bases include amines and nitrogen containing heterocycles, in particular, 1,4-diazabicyclo [2.2.2]octane.

A transdermal delivery device in accordance with the invention can be prepared by dissolving the copolymer, the enhancer (if present), and the lerisetron in an organic solvent (e.g., ethyl acetate) to provide a coating formulation. The coating formulation can be coated onto a suitable release liner using conventional methods to provide a predetermined uniform thickness of the coating formulation. Suitable release liners include conventional release liners comprising a known sheet material such as a polyester web, polyethylene web, or a polystyrene web, or a polyethylene-coated paper coated with a suitable fluoropolymer or silicone based coating. Preferred release liners include 1-5PESTR(P2)-164P, 1-5PESTR(MATTE)-164Z from DCP-Lohja Inc or ScotchPak™ 1022 from 3M, St. Paul, Minn.

The coated release liner is then dried and laminated onto a backing using conventional methods. The backing can be occlusive, non-occlusive or a breathable film as desired. The backing is flexible such that it conforms to the skin. It can be any of the conventional materials for pressure sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the composition. Particularly preferred backings are COTRAN™ 9726, COTRAN™ 9720, and CoTran™ 9722 all available from 3M.

The transdermal delivery devices can be made in the form of an article such as a tape, a patch, a sheet, a dressing or any other form known to those skilled in the art. Generally, the device will be in the form of a patch of a size suitable to deliver a preselected amount of lerisetron through the skin. Generally, the device will have a surface area of about 10 $cm^2$ to about 140 $cm^2$ and preferably about 20 $cm^2$ to about 80 $cm^2$.

A transdermal drug delivery composition of the invention can be used to treat any condition capable of treatment with lerisetron and in particular, the prevention or treatment of nausea and emesis. The composition can be placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

The examples set forth below are intended to illustrate the invention, and not to be limiting in any way.

EXAMPLES

In Vitro Skin Penetration Test Method

The skin penetration data given in the examples below was obtained using the following test method. A static diffusion cell (Franz-cell type) is used. Hairless mouse skin (female hairless mice, 3–4 weeks old) or human skin (obtained from surgery) is used. The skin is mounted epidermal side up between the upper and the lower portion of the cell, which are held together by means of a ball joint clamp.

The portion of the cell below the mounted skin is completely filled with receptor fluid ["HEPES" (N-[2-hydroxyethyl]piperazine-N'-[2-ethanesulfonic acid]) buffered Hanks balanced salt solution, pH 7.2, supplemented with 4 ml of antibiotics (A 7292 obtained from Sigma) and 15-volume-% ethanol (extra pure grade, 96%) per liter] such that the receptor fluid is in contact with the skin. The receptor fluid is stirred using a magnetic stir bar. The sampling port is covered except when in use.

When a transdermal delivery device is evaluated, the release liner is removed from a 1.55 $cm^2$ patch and the patch is applied to the skin and pressed to cause uniform contact with the skin. The skin is then placed across the orifice of the lower portion of the diffusion cell. The diffusion cell is assembled and the lower portion is filled with receptor fluid.

The cell is then placed in a constant temperature (32±1.5° C.) and humidity (45±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (2, 4, 6, 8, and 24 hours) and immediately replaced with fresh receptor fluid. The withdrawn receptor fluid is analyzed for drug content using conventional high performance liquid chromatography. The cumulative amount of drug penetrating the skin and the flux rate are calculated.

Stability Test Method

Transdermal drug delivery devices (10 $cm^2$ patches) were sealed in pouches (BAREX™/aluminum/polyester or BAREX™/aluminum/paper laminates) and stored at 25° C./60% relative humidity and 40° C./75% relative humidity.

The patches were analyzed for their drug content before storage and after 2 and 4 weeks storage time. The drug content was determined by removing the liner from the patches. The backing and coating were extracted using 40.0 ml of ethyl acetate. The sample was shaken for approximately 2 hr. A portion (2.0 ml) of the ethyl acetate solution was pipetted into a 50.0 ml volumetric flask and diluted to mark with mobile phase (a solution containing acetonitrile and 0.01M triethylamine in water in the ratio of 60:40 (vol-%) having a pH of about 6.5). An aliquot of the solution was transferred into a tube and centrifuged at 4300 rpm for 10 minutes. The sample was placed in a vial and injected into an HPLC equipped with a Spherisorb™ C8 column. Quantification was performed by external standard methodology (peak area) using a UV-detector working at 282 nm.

The abbreviations listed below are used in the examples.

IOA: isooctyl acrylate

NVP: N-vinyl-2-pyrrolidone

HEA: 2-hydroxyethyl acrylate

IPM: isopropyl myristate

PG: propylene glycol

OA: oleic acid

LA: lauric acid

ELVACITE™: polymethylmethacrylate macromonomer available from ICI Acrylics

DCP-Lohja 164Z: release liner 1-5PESTR(MATTE)-164Z release liner available from

DCP-Lohja Inc.

Preparation of the Copolymers

The inherent viscosity values which are reported below were measured by conventional means using a Canon-Fenske #50 viscometer in a water bath controlled at 27° C. to measure the flow time of 10 millimeters of the polymer solution (0.15 g of polymer per deciliter of ethyl acetate). The test procedure and apparatus are described in detail in *Textbook of Polymer Science*, F. W. Billmeyer, Wiley Interscience, Second Edition (1971), pages 84 and 85.

Preparation of Isooctyl Acrylate/N-Vinyl-2-pyrrolidone/Elvacite™ 1020 (77/20/3) Copolymer A flask equipped with an agitator, condenser, nitrogen inlet tube and an addition funnel was charged with isooctyl acrylate (134.75 g), N-vinyl-2-pyrrolidone (35.0 g) and Elvacite™ 1020 (5.25 g) premixed in a mixture of ethyl acetate (236.25 g) and methanol (26.25 g). The mixture was heated to 60° C. with medium agitation and purged with nitrogen to remove oxygen. 2,2'-Azobis-(2-methylbutyronitrile) (0.26 g, Wako™ V-59) was added to initiate reaction. The reaction temperature was maintained at 57° C.

and the reaction was run for about 24 hours. After termination of the reaction additional ethyl acetate (90 g) and methanol (10 g) were added. The inherent viscosity was 1.4 dl/g.

Preparation of Isooctyl Acrylate/2-Hydroxyethyl acrylate/Elvacite™ 1020 (59/39/2) Copolymer This copolymer was prepared using a procedure similar to the one described above for isooctyl acrylate/N-vinyl-2-pyrrolidone/Elvacite™ 1020. The inherent viscosity of the polymer in ethyl acetate was 0.69 dl/g.

Preparation of Isooctyl acrylate/2-Hydroxyethyl acrylate/N-vinyl-2-pyrrolidone (89/2/9) Copolymer A flask equipped with an agitator, condenser, nitrogen inlet tube and an addition funnel was charged with isooctyl acrylate (155.75 g), N-vinyl-2-pyrrolidone (15.75 g) and hydroxyethyl acrylate (3.50 g) premixed in a mixture of ethyl acetate (249.38 g) and methanol (13.13 g). 2,2'-Azobis-(2-methyl-butyronitrile) (0.26 g, Wako™ V-59) was added to initiate reaction. The mixture was purged with nitrogen to remove oxygen. The mixture was agitated and heated to 57° C. and the reaction was run for about 24 hours at this temperature. After termination of the reaction additional ethyl acetate (178.13 g) and methanol (9.38 g) were added. The inherent viscosity was 1.27 dl/g.

EXAMPLE 1

To 48.74 g of a solution containing 39% by weight of IOA/HEA/Elvacite 59/39/2 in ethyl acetate there were added 0.68 g OA, 6.12 g PG and a solution of 6.29 g of lerisetron in 8.2 g of methanol. Intensive mixing provided a homogeneous coating solution.

The solution was coated onto a release liner (DCP-Lohja 164Z) and oven dried for 20 minutes at 60° C. The dried coating was then laminated to a CoTran™ 9720 backing. The resulting devices had a drug loading of 2.37 mg lerisetron per 1 $cm^2$.

EXAMPLE 2

To 69.13 g of a solution containing 28% by weight of IOA/NVP/Elvacite 77/20/3 in ethyl acetate there were added, 0.53 g LA, 10.07 g PG and a solution of 2.21 g lerisetron in 6.23 g methanol. Intensive mixing provided a homogeneous coating solution.

The solution was coated onto a release liner (DCP-Lohja 164Z) and oven dried for 20 minutes at 60° C. The dried coating was then laminated to a CoTran™ 9720 backing. The resulting devices had a drug loading of 0.48 mg lerisetron per 1 $cm^2$.

EXAMPLE 3

To 37.73 g of a solution containing 28% by weight of IOA/NVP/Elvacite 77/20/3 in ethyl acetate there were added 0.45 g LA, 4.08 g 1,3-butandiol and a solution of 1.60 g lerisetron in 3.4 g methanol. Intensive mixing provided a homogeneous coating solution.

The solution was coated onto a release liner (DCP-Lohja 164Z) and oven dried for 20 minutes at 60° C. The dried coating was then laminated to a CoTran™ 9720 backing. The resulting devices had a drug loading of 0.75 mg lerisetron per 1 $cm^2$.

EXAMPLE 4

To 34.50 g of a solution containing 39% by weight of IOA/HEA/Elvacite 59/39/2 in ethyl acetate there was added a solution of 2.19 g lerisetron in 4.67 g methanol. Intensive mixing provided a homogeneous coating solution.

The solution was coated onto a release liner (DCP-Lohja 164Z) and oven dried for 20 minutes at 60° C. The dried coating was then laminated to a CoTran™ 9720 backing. The resulting devices had a drug loading of 1.47 mg lerisetron per 1 $cm^2$.

EXAMPLE 5

To 35.70 g of a solution containing 28% by weight of IOA/NVP/HEA 89/9/2 in ethyl acetate there were added 0.65 g LA, 5.85 g PG and a solution of 1.64 g lerisetron in 3.20 g methanol. Intensive mixing provided a homogeneous coating solution.

The solution was coated onto a release liner (DCP-Lohja 164Z) and oven dried for 20 minutes at 60° C. The dried coating was then laminated to a CoTran™ 9720 backing. The resulting devices had a drug loading of 0.66 mg lerisetron per 1 $cm^2$.

EXAMPLE 6

To 67.48 g of a solution containing 28% by weight of IOA/NVP/Elvacite 77/20/3 in ethyl acetate there were added 0.55 g of 4.3% by weight of 1,4-diazabicyclo[2.2.2]octane in ethyl acetate, 0.50 g LA, 9.50 g PG and a solution of 2.20 g lerisetron in 6.01 g methanol. Intensive mixing provided a homogeneous coating solution.

The solution was coated onto a release liner (ScotchPak™ 1022) and oven dried for 20 minutes at 60° C. The dried coating was then laminated to a CoTran™ 9722 backing. The resulting devices had a drug loading of 0.69 mg lerisetron per 1 $cm^2$.

EXAMPLE 7

To 68.20 g of a solution containing 28% by weight of IOA/NVP/Elvacite 77/20/3 in ethyl acetate there were added 0.55 g of 4.3% by weight of 1,4-diazabicyclo[2.2.2]octane in ethyl acetate, 5.76 g IPM and a solution of 1.50 g lerisetron in 5.44 g methanol. Intensive mixing provided a homogeneous coating solution.

The solution was coated onto a release liner (ScotchPak™ 1022) and oven dried for 20 minutes at 60° C. The dried coating was then laminated to a CoTran™ 9722 backing. The resulting devices had a drug loading of 0.62 mg lerisetron per 1 $cm^2$.

EXAMPLE 8

To 67.92 g of a solution containing 28% by weight of IOA/NVP/Elvacite 77/20/3 in ethyl acetate there were added 0.55 g of 4.3% by weight of 1,4-diazabicyclo[2.2.2]octane in ethyl acetate, 10.24 g PG and a solution of 2.22 g lerisetron in 6.02 g methanol. Intensive mixing provided a homogeneous coating solution.

The solution was coated onto a release liner (ScotchPak™ 1022) and oven dried for 20 minutes at 60° C. The dried coating was then laminated to a CoTran™ 9722 backing. The resulting devices had a drug loading of 0.68 mg lerisetron per 1 $cm^2$.

EXAMPLE 9

To 29.98 g of a solution containing 24% by weight of IOA/NVP/Elvacite 77/20/3 in ethyl acetate there were added 0.09 g LA, 3.34 g PG and a solution of 0.80 g lerisetron in 1.87 g methanol. Intensive mixing provided a homogeneous coating solution.

The solution was coated onto a release liner (DCP-Lohja 164P) and oven dried for 20 minutes at 60° C. The dried coating was then laminated to a CoTran™ 9726 backing. The resulting devices had a drug loading of 0.66 mg lerisetron per 1 cm².

EXAMPLE 10

To 30.13 g of a solution containing 24% by weight of IOA/NVP/Elvacite 77/20/3 in ethyl acetate there were added 0.67 g OA, 2.68 g PG and a solution of 0.68 g lerisetron in 1.60 g methanol. Intensive mixing provided a homogeneous coating solution.

The solution was coated onto a release liner (DCP-Lohja 164P) and oven dried for 20 minutes at 60° C. The dried coating was then laminated to a CoTran™ 9720 backing. The resulting devices had a drug loading of 0.74 mg lerisetron per 1 cm².

The transdermal drug delivery devices prepared in Examples 1–10 were tested using the skin penetration test method described above. The results are shown in Table 1 below where each entry is the average of four independent determinations.

TABLE 1

Skin Penetration

| Example | Copolymer | Enhancers[1] (wt-%) | Coating Weight (mg/cm²) | Drug loading (mg/cm²) | Flux Rate (μg/cm²/24 hr) |
|---|---|---|---|---|---|
| 1 | IOA/HEA/ELV 59/39/2 | 20% PG 2% OA | 11.9 | 2.37 | 61 |
| 2 | IOA/NVP/ELV 77/20/3 | 32% PG 2% LA | 6.8 | 0.48 | 132 |
| 3 | IOA/NVP/ELV 77/20/3 | 25% 1,3-Butandiol 3% LA | 7.5 | 0.75 | 128 |
| 4 | IOA/HEA/ELV 59/39/2 | — | 7.0 | 1.47 | 65 |
| 5 | IOA/NVP/HEA 89/9/2 | 32% PG 4% LA | 7.4 | 0.66 | 178 |
| 6 | IOA/NVP/ELV 77/20/3 | 30% PG 2% LA | 9.8 | 0.69 | 199 |
| 7 | IOA/NVP/ELV 77/20/3 | 22% IPM | 11.0 | 0.62 | 129 |
| 8 | IOA/NVP/ELV 77/20/3 | 32% PG | 9.6 | 0.68 | 131 |
| 9 | IOA/NVP/ELV 77/20/3 | 29% PG 1% LA | 9.4 | 0.66 | 177 |
| 10 | IOA/NVP/ELV 77/20/3 | 24% PG 6% OA | 12.3 | 0.74 | 272 |

[1]weight % of enhancer based on the total weight of solids

The transdermal drug delivery devices prepared in Examples 6, 9 and 10 were tested for stability using the test method described above. The results are shown in Table 2 below.

TABLE 2

Stability Data

| Example No. | Drug content after 2 weeks* | Drug content after 4 weeks* |
|---|---|---|
| 6 | 101.2 | 99.9 |
| 9 | 102.1 | 102.7 |
| 10 | 98.2 | 99.5 |

*Drug content is reported as the percentage remaining of the original drug loading; the accuracy of the data is +/-2 to 3%.

What is claimed is:

1. A transdermal drug delivery composition comprising:
(a) a copolymer of one or more (meth)acrylate monomers being selected from the group consisting of alkyl acrylates containing 4 to 12 carbon atoms in the alkyl group and alkyl methacrylates containing 4 to 12 carbon atoms in the alkyl group and one or more hydrophilic monomers being copolymerizable with said (meth)acrylate monomers, and
(b) a therapeutically effective amount of lerisetron.

2. A transdermal drug delivery composition of claim 1 further comprising a penetration enhancer.

3. A transdermal drug delivery composition of claim 2 wherein said penetration enhancer is selected from the group consisting of alkane polyols, fatty acids, fatty acid esters, fatty alcohols, and $C_5$–$C_{18}$ alkyl esters of a carboxylic acid, and mixtures thereof.

4. A transdermal drug delivery composition of claim 3 wherein the alkane polyol is propylene glycol and the fatty acid is oleic acid or lauric acid.

5. A transdermal drug delivery composition of claim 2 wherein the enhancer is present in an amount of from about 10 to about 50 percent by weight based on the total weight of the composition.

6. A transdermal drug delivery composition of claim 5 wherein the enhancer is present in an amount of from about 20 to about 35 percent by weight based on the total weight of the composition.

7. A transdermal drug delivery composition of claim 1 wherein the lerisetron is present in an amount of from about 2 to about 20 percent by weight based on the total weight of the composition.

8. A transdermal drug delivery composition of claim 7 wherein the lerisetron is present in an amount of from about 5 to about 10 percent by weight based on the total weight of the composition.

9. A transdermal drug delivery composition of claim 1 wherein the lerisetron is dissolved in the composition.

10. A transdermal drug delivery composition of claim 1 wherein the acrylate monomer is selected from the group consisting of isooctyl acrylate, 2-ethylhexyl acrylate, cyclohexyl acrylate and n-butyl acrylate, and mixtures thereof.

11. A transdermal drug delivery composition of claim 10 wherein the acrylate monomer is isooctyl acrylate.

12. A transdermal drug delivery composition of claim 1 wherein the hydrophilic monomer is selected from the group consisting of 2-hydroxyethyl acrylate, N-vinyl-2-pyrrolidone, acrylic acid, and mixtures thereof.

13. A transdermal drug delivery composition of claim 1 wherein the hydrophilic monomer is N-vinyl-2-pyrrolidone.

14. A transdermal drug delivery composition of claim 1 wherein the copolymer further comprises one or more substantially linear macromonomers copolymerizable with the (meth)acrylate and hydrophilic monomers.

15. A transdermal drug delivery composition of claim 14 wherein the macromonomer is selected from the group consisting of polymethylmethacrylate, styrene/acrylonitrile, polyether and polystyrene macromonomers.

16. A transdermal drug delivery composition of claim 15 wherein the macromonomer is polymethylmethacrylate.

17. A transdermal drug delivery composition of claim 14 wherein the copolymer comprises from about 55 to 90 percent by weight of (meth)acrylate monomers, from about 7 to about 40 percent by weight of hydrophilic monomers, and from about 1 to about 7 percent by weight of macromonomers based on the total weight of the copolymer.

18. A device for the transdermal delivery of lerisetron comprising a backing having a composition adhered to one surface of the backing, said composition comprising
    (a) a copolymer of one or more (meth)acrylate monomers being selected from the group consisting of alkyl acrylates containing 4 to 12 carbon atoms in the alkyl group and alkyl methacrylates containing 4 to 12 carbon atoms in the alkyl group and one or more hydrophilic monomers being copolymerizable with said (meth)acrylate monomers, and
    (b) a therapeutically effective amount of lerisetron.

19. A method of transdermal delivery of lerisetron to a mammal comprising the steps of:
    (a) providing a composition according to claim 1;
    (b) placing the composition on the skin of a mammal; and
    (c) allowing the composition to remain on the skin for a time sufficient to allow lerisetron to penetrate the skin of the mammal.

20. A method of treating in a mammal a condition capable of treatment by lerisetron comprising the steps of:
    (a) providing a composition according to claim 1;
    (b) placing the composition on the skin of a mammal; and
    (c) allowing the composition to remain on the skin for a time sufficient to establish or maintain a therapeutically effective blood level of lerisetron in the mammal.

21. A method of preventing and/or treating nausea and emesis in a mammal comprising the steps of:
    (a) providing a composition according to claim 1;
    (b) placing the composition on the skin of a mammal; and
    (c) allowing the composition to remain on the skin for a time sufficient to establish or maintain a therapeutically effective blood level of lerisetron in the mammal.

* * * * *